(12) United States Patent
Pon et al.

(10) Patent No.: US 6,624,885 B1
(45) Date of Patent: Sep. 23, 2003

(54) METHOD AND DEVICE FOR NON-DESTRUCTIVE ANALYSIS OF PERFORATION IN A MATERIAL

(75) Inventors: Russell M. Pon, Danville, CA (US); Rajesh S. Patel, Fremont, CA (US); James M. Bovatsek, San Jose, CA (US); Jeffrey A. Schuster, Berkeley, CA (US); Geoffrey K. McKinley, Palo Alto, CA (US); Sze-The Young, San Jose, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

(21) Appl. No.: 09/330,254

(22) Filed: Jun. 10, 1999

(51) Int. Cl.⁷ .............................................. G01N 21/00
(52) U.S. Cl. .................................................. 356/237.6
(58) Field of Search ........................... 356/237.1, 237.2, 356/241.1, 237.6

(56) References Cited

U.S. PATENT DOCUMENTS

| | | | | |
|---|---|---|---|---|
| 3,711,205 A | * | 1/1973 | Tulk et al. | 356/162 |
| 3,806,252 A | * | 4/1974 | Harris et al. | 356/156 |
| 4,596,037 A | * | 6/1986 | Bouchard et al. | 382/8 |
| 4,647,208 A | * | 3/1987 | Bieman | 356/375 |
| 4,930,889 A | * | 6/1990 | Van Donselaar et al. | 356/237 |
| 5,497,764 A | | 3/1996 | Ritson et al. | 128/200.14 |
| 5,528,359 A | * | 6/1996 | Taguchi | 356/237 |
| 5,544,646 A | | 8/1996 | Lloyd et al. | 128/200.14 |
| 5,660,166 A | | 8/1997 | Lloyd et al. | 128/200.14 |
| 5,709,202 A | | 1/1998 | Lloyd, et al. | 128/200.14 |
| 5,718,222 A | | 2/1998 | Lloyd et al. | 128/200.14 |
| 5,745,168 A | * | 4/1998 | Ninomiya | 348/191 |
| 5,823,178 A | | 10/1998 | Lloyd et al. | 128/200.14 |
| 5,829,435 A | | 11/1998 | Rubsamen et al. | 128/203.21 |
| 6,140,604 A | * | 10/2000 | Somers et al. | 219/121.71 |
| 6,441,340 B1 | * | 8/2002 | Varriano-Marston | 219/121.7 |

* cited by examiner

*Primary Examiner*—Michael P. Stafira
(74) *Attorney, Agent, or Firm*—Karl Bozicevic; Bozicevic, Field & Francis LLP (57) ABSTRACT

A method for inspecting small holes in a material is disclosed. The method comprises directing a light source through the holes in the material, and then focusing the light passing through the material onto a CCD detector. The focusing techniques allow for a reduction in the size of the image which must be inspected, thereby increasing sample throughput, while still allowing for detailed inspection of the hole number and quality. Methods of producing an aerosolization container and device comprising membranes which pass such an inspection are also provided.

50 Claims, 2 Drawing Sheets

METHOD AND DEVICE FOR NON-DESTRUCTIVE ANALYSIS OF PERFORATION IN A MATERIAL

FIELD OF THE INVENTION

The invention relates generally to methods of non-destructive analysis. More particularly, the invention relates to a method and device for quickly and non-destructively analyzing an array of small holes precisely placed in a material such as a thin film.

BACKGROUND OF THE INVENTION

In different areas of technology it is desirable to make use of a thin sheet of material which has an array of regularly spaced, very small holes therein. For example, such might be used in the manufacture of various electronic components. Thin membranes which have one or more holes in them could also be used in the formation of components used in ink jet printers or fuel injectors. A more direct application of such a porous membrane is as a filter. The pore size and pore density could be adjusted to wide range of filter applications. Alternatively, liquid formulations containing a drug could be moved through such a porous member to create an aerosol for inhalation.

One of the gentlest and most acceptable methods of administering an agent to a patient is via aerosol. Aerosol therapy can be accomplished by aerosolization of a formulation (e.g., a drug formulation or diagnostic agent formulation) and administration to the patient, for example via inhalation. The aerosol can be used to treat lung tissue locally and/or be absorbed into the circulatory system to deliver the drug systemically. Where the formulation contains a diagnostic agent, the formulation can be used for diagnosis of, for example, conditions and diseases associated with pulmonary dysfunction.

In general, aerosolized particles for respiratory delivery must have a diameter of 12 microns or less. However, the preferred particle size varies with the site targeted (e.g, delivery targeted to the bronchi, bronchia, bronchioles, alveoli, or circulatory system). For example, topical lung treatment can be accomplished with particles having a diameter in the range of 1.0 to 12.0 microns. Effective systemic treatment requires particles having a smaller diameter, generally in the range of 0.5 to 6.0 microns, while effective ocular treatment is adequate with particles having a diameter of 15 microns or greater, generally in the range of 15–100 microns.

U.S. Pat. No. 5,544,646, 5,709,202, 5,497,763, 5,544,646, 5,718,222, 5,660,166, 5,823,178 and 5,829,435 describe devices and methods useful in the generation of aerosols suitable for drug delivery. These devices generate fine, uniform aerosols by passing a formulation through a porous membrane having micron-scale pores as may be formed, for example, by laser ablation.

Porous membranes having such small features are difficult and costly to manufacture. Additionally, the pores must be of high quality and uniformity where they are to be used (1) in manufacturing electronic components; (2) in filter materials; (3) in ink jet printers; (4) in fuel injectors; and (5) to create aerosols for delivering therapeutic agents to patients in order to insure that the patients consistently receive the therapeutically required dose. Consequently, there is a need for an inspection method which can rapidly analyze porous samples of small dimensions to determine various parameters including pore size and pore density.

SUMMARY OF THE INVENTION

Thin films having small holes therein (porous membranes) are inspected or non-destructively analyzed by (1) shining a light through the pores of the membrane (2) detecting light which has passed through the pores and (3) analyzing the detected light in a manner which makes it possible to quickly determine whether the membrane should "pass" inspection based on criteria such as pore size and pore density. The device used in the inspection must include (1) a light source (2) a light detector and (3) a means for analyzing the detected light. Other components may be and generally are present such as light filters and lens for improving the overall accuracy of the system and a means for moving membranes into and out of position to improve the overall efficiency of the system.

The inspection system of the invention can carry out non-destructive inspection for the presence of microscopic pores within a thin film and determine the characteristics of the porous membrane including the pore size and shape, pore density and overall acceptability of the porous membrane. The system includes the ability to detect the light transmitted through the holes within the membrane and utilize the detected light information to develop a relationship between the level of light and the size and shape of the hole, i.e. light levels detected from each hole-feature can be related to the individual size or shape of the hole. Further, the light levels from an entire array of pores within a membrane can be related to the collective average size and/or shapes of the holes. If the pores within the membrane do not meet a required criteria an alarm can be triggered at a given threshold level indicating that the porous membrane being tested does not have an adequate number of holes having the desired size and/or shape. Such an evaluation is preferably made on an overall reading of the porous membrane. More specifically, light is shown on the porous membrane and allowed to move through the holes to a detector. If a desired quantity of light is not detected by the detector there are either an insufficient number of holes or the holes are of insufficient size or some combination of both. Further, if too much light is detected than either the holes are too large or there are too many holes present in the membrane. Falling above or below the detected amount of light triggers an alarm which causes the porous membrane being inspected to be rejected.

The system is capable of being used in connection with a variety of different porous membranes. The pores can have different sizes or shapes and can be present on the membrane in a variety of different patterns and pore densities. These different membranes with different patterns and pore sizes can be detected using the same charge-coupled light detector element and processed using the same microprocessor unit. If necessary the system can utilize a variety of different components including mirrors, rhomboids, wedges, or combinations thereof in order to obtain the desired results with a given porous membrane of the same basic components of the inspection system.

The inspection system of the invention can be used to check all of the porous membranes produced by a given production system or used to spot check a certain percentage amount of those porous membranes. Further, the system can be integrated into a production system so that membranes are inspected at a given point before being used in an assembly process to produce a component which includes a porous membrane. When utilized in this manner the porous membrane need not be removed from the system for inspection purposes. Light transmitted through the pores of the membrane can be detected and used as a trigger to accept or reject the porous membrane for further use in the manufacturing process.

Porous membranes which are inspected using the present invention can be produced using focused laser light to create the pores in the membrane. The present system can utilize the light from the laser in order to carry out the inspection in real time. More specifically, the laser light used in order to create the holes can be detected by the detector and used to determine if the holes have been made, made in sufficient size and sufficient pore density. Further, the system of the invention can be used to assist in production. For example, if the laser light used in making the holes in the membrane is detected the detection of a certain amount of light can signal that the hole is sufficiently large thereby signaling that the laser light should be discontinued in order to prevent the hole from being made too large.

The present invention rapidly inspects samples for holes or through features at the micron and submicron level. This method can be used to inspect previously manufactured samples, or can be integrated into the manufacturing process in order to allow for concurrent production and inspection of samples containing such features. In one aspect of the invention, an imaging lens is used to reduce the size of the image which must be inspected, allowing for more rapid inspection and requiring a smaller CCD detector and shorter analysis time of the smaller image.

An aspect of the invention is a method of analyzing a porous membrane which involves directing light onto a porous membrane, detecting light passing through pores of the membrane and then analyzing the detected light in a manner which determines if the pores of the membrane meet desired criteria.

Another aspect of the invention is a method of analyzing a porous membrane by directing light onto the porous membrane, detecting light reflecting off of the membrane and analyzing the reflected light in a manner such that the analysis determines if pores of the membrane meet a desired criteria.

Another aspect of the invention is an analysis system which includes a means for directing light onto a porous membrane, a means for detecting light which is reflected off of and/or light which passes through pores of the membrane and a means for analyzing either the reflected light and/or the light passing through pores of the membrane so as to determine if pores of the membrane meet a desired criteria.

A preferred aspect of the invention includes a means for moving one porous membrane after another into position for analysis or moving the system relative to the membranes in order to continuously analyze one membrane after another.

In another aspect of the invention, a film, e.g. a polyimide film containing laser-ablated pores which has been inspected to determine the number and size of the pores.

In still another aspect of the invention, the light source employed produces ultraviolet light which is selectively transmitted through the features in the inspected sample.

In an additional aspect of the invention, a method of producing an aerosolization container comprising an aerosolization nozzle passing the inspection method is provided.

In a further aspect of the invention, a method of producing an aerosolization device comprising such a container is also provided.

An advantage of the invention is that porous membranes can be quickly, accurately and efficiently inspected.

A feature of the invention is that different types of light sources can be used and different types of filters can be used and positioned differently relative to the membrane being inspected.

Another feature of the invention is that the membrane may be moved relative to the light source and detector or the light source and/or detector may be moved relative to the membrane.

These and other aspects, objects, advantages and features of the present invention will become apparent to those skilled in the art upon reading this disclosure and reviewing the drawings forming a part hereof

BRIEF DESCRIPTION OF THE DRAWINGS

FIG. 1 is a schematic drawing of the system used to inspect samples for the size and number of holes passing through the sample.

FIG. 2 shows optical images from samples which pass inspection following the inspection method.

FIG. 3 shows optical images of samples which do not pass inspection from the inspection method.

DESCRIPTION OF THE PREFERRED EMBODIMENTS

Before the present methods and systems of detecting and analyzing the holes are disclosed, it is to be understood that this invention is not limited to the particular methodology and devices described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an analyzing means" includes one or more of such means, and reference to "the method" or "the step" includes reference to equivalent steps and methods known to those skilled in the art, and so forth.

Where a range of values is provided, it is understood that each intervening value between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller range is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited.

The publications discussed above are provided solely for their disclosure prior to the filing date of the present application. Nothing herein is to be construed as an admission that the invention is not entitled to antedate such disclosure by virtue of prior invention.

DEFINITIONS

The term "porosity" is used herein to mean a percentage of an area of a surface area that is composed of open space, e.g., a pore, hole, channel or other opening, in a membrane, nozzle, filter or other material. The percent porosity is thus defined as the total area of open space divided by the area of the material, expressed as a percentage (multiplied by 100). High porosity (e.g., a porosity greater than 50%) is associated with high flow rates per unit area and low flow resistance. In general, the porosity of the nozzle is less than 10%, and can vary from $10^{-5}\%$ to 10%, while the porosity of the filter is at least 1%, and preferably at least 50%, porous. Porous membranes of the invention may have any porosity without limitation. Further, a porous membrane may have any number of pores, any pore density or pore size. For example, a membrane may have a single pore which can range considerably in size or have thousands of pores each of which could be the same or different in size and range considerably in size.

The term "porous membrane" will be interpreted to mean any membrane having any number of holes therein. However, there are a number of types of preferred membranes which the system and method of the invention are particularly useful for inspecting. Thus, the porous membrane may mean a membrane of material having any given outer parameter shape (may have a planar or a convex shape), wherein the membrane has one pore or a plurality of pores therein, which openings may be placed in a regular or irregular pattern, and which pores have an unflexed diameter of their exit aperture in the range of 0.01 micron to 100 microns and a pore density in the range of 1 to 1,000 pores per square millimeter for respiratory delivery. For ocular delivery, the pores have an unflexed diameter of their exit aperture in the range of 5 microns to 50 microns, preferably 7.5 to 25 microns, and a similar pore density. The porous membrane has a porosity of about 0.0005% to 0.2%, preferably about 0.01% to 0.1%. In one embodiment, the porous membrane comprises a single row of pores on, e.g., a large piece of membrane material. The pores may be planar with respect to the surface of the porous membrane material, or may have a conical configuration. The membrane material is preferably hydrophobic and includes materials such as polycarbonates, polyimides, polyethers, polyether imides, polyethylene and polyesters which may have the pores formed therein by any suitable method including laser drilling or anisotropic etching through a thin film of metal or other suitable material. The membrane preferably has sufficient structural integrity so that it is maintained intact (will not rupture) when subjected to force in the amount up to about 40 bar, preferably of up to about 50 bar while the formulation is forced through the pores.

GENERAL OVERVIEW OF THE INVENTION

The invention provides a method of rapidly inspecting and analyzing multiple holes or through features present in a sample. The method comprises directing a light source producing a wavelength of light which is absorbed by the sample material, but which passes through the holes or through features and is detected by a charge-coupled device. An imaging lens can be used to reduce the size of the image, thereby reducing analysis time and increasing throughput. This inspection method can be integrated into the manufacturing of porous membranes for a variety of uses.

Figure 1:
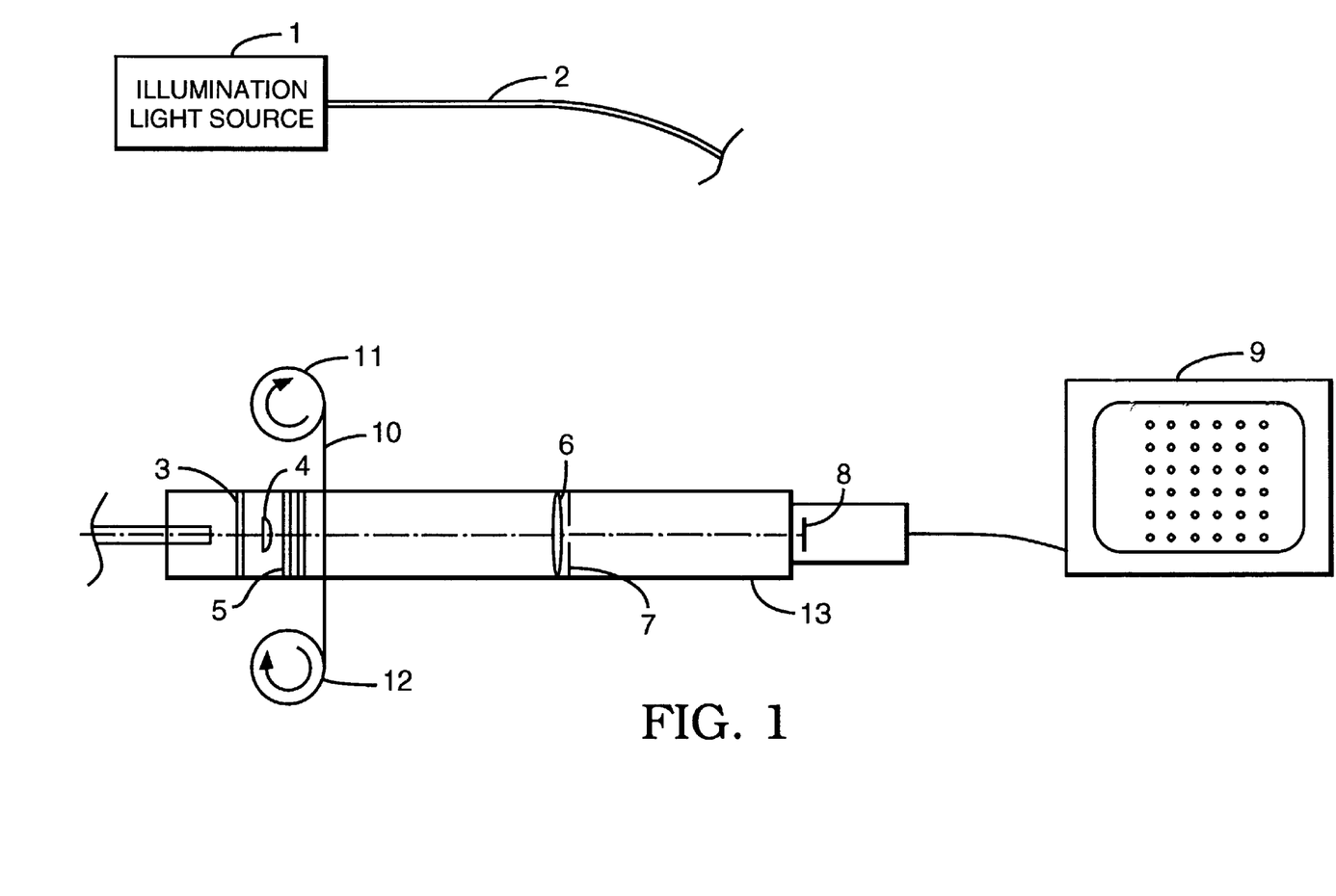
Figure 2:
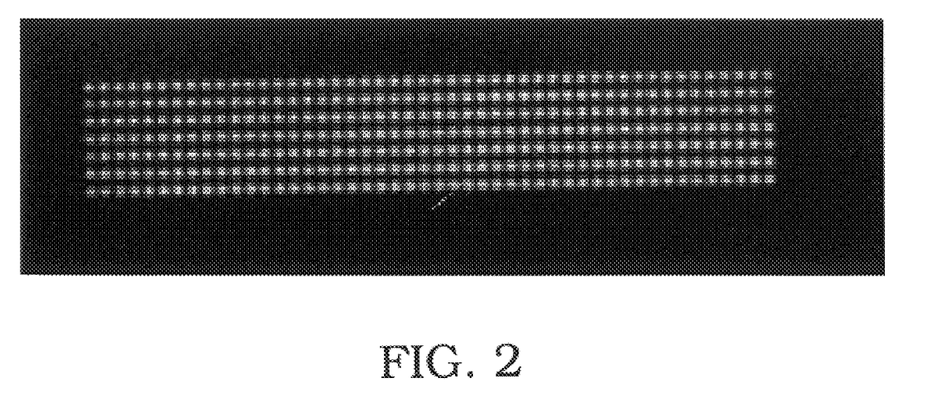
Figure 3:
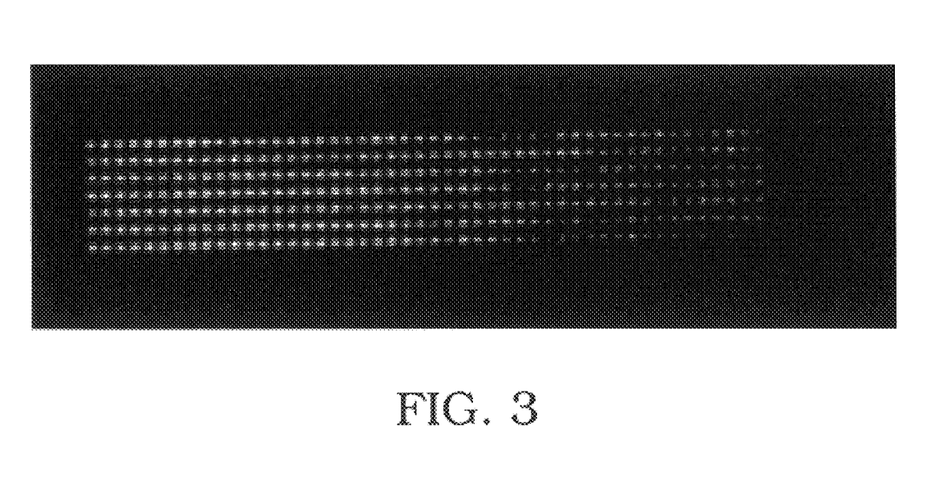

FIG. 1 is a view of a schematic representation of the inspection system of the invention. The light source 1 is chosen based on a variety of criteria relating to factors such as how the wave length of light emitted by the source will be effected by the material of the porous membrane 10 being inspected. Light from the source 1 may shine directly on the membrane 10 but is preferably directed through a light guide 2 e.g. optical fiber or optical fibers. Light emitted from the light guide 2 may shine directly on the membrane 2 but is preferably directed through all or any of an optical diffuser 3, illuminated lens 4 and one or more spectral filters 5.

The light exiting the spectral filters 5 shines on the porous membrane 10. Substantially all if not all of the light striking the membrane is either absorbed or reflected and therefore does not travel through the membrane 10 unless the light enters one of the pores of the porous membrane. Light entering a pore is transmitted and strikes the light detector 8 which is preferably in the form of a charge-coupled device (CCD). Before contacting the light detector 8 the light may pass through an imaging lens 6 and an aperture stop 7. Once a porous membrane 10 has been inspected it is preferable to simply rotate a cylinder 11 containing new porous membranes and wind up the inspected membranes on the cylinder 12. In this manner one porous membrane after another can be inspected thereby providing an efficient inspection system.

All of the light exiting the pores of the porous membrane 10 is preferably contained within a light containment tube 13. This allows for an improved signal and also improves the stray light which might effect the signal on the light detector 8. After light has been detected on the light detector 8 the signal obtained is transmitted to a microprocessor 9 which carries out computer image analysis. The processing can be carried out in a variety of different ways and can focus on individual pores of the membrane or, more preferably, on the total signal received. If the total signal received is too small than the pores are.insufficiently large or present in an insufficient pore density. If the signal received is too large than the pores are too large or are present in an excessive pore density. Regardless of the criteria set once an analysis is made then the system provides a signal as to whether the porous membrane being inspected passes inspection or should be rejected.

SYSTEM COMPONENTS

The basic components of the system are shown in FIG. 1. However, of these components it is necessary to include the light source 1, detection means 8 and microprocessor analyzing means 9. The other components are preferably used in order to increase the accuracy and efficiency of the system. Most importantly, the system preferably includes a means for moving one sample membrane 10 after another into position for inspection. Each of the components as shown in FIG. 1 will now be described in further detail.

The illumination light source 1 can be a commercially purchased light source sold under the trade name Ultracure 100SS Plus. The light source is a 100 watt mercury lamp system typically used in UV-curing applications. Mercury lamps typically emit strong spectral components at about 365 nm which is strongly absorbed by polyimide film having a thickness of microns which film is sold by DuPont under the tradename Kapton. The light source does emit spectral peaks in the 300–400 nm region and has a useful spectral range of light of wavelengths less than 450 nm. The light having a wavelength of less than 450 nm is absorbed in the top few microns of the film which is 25 microns thick. Wavelengths longer than 550 nm are not absorbed at all but would be transmitted through the film. The combination of illumination and wavelength absorbed by the film determines the contrast between light transmitted through the film and light transmitted through the holes. Films can be used where all of the light is absorbed. Further, detectors can be used where wavelengths of light which pass through the film are not detected by the detector 8. The greater the contrast produced between light passing through the pores and light passing through the film, the more robust the image processing algorithms for image analysis.

Although essentially any type of light source can be used arc lamps are preferred and are characteristically small sources of light which enable more efficient focusing and collimation of the light. This makes it possible to transmit light into a light guide and also makes it possible to obtain relatively good collimation of the light emitted from the light guide. Collimated light on the inspection sample insures that the illuminated incident light is at the same angle for each hole in the film. If light were shown on the film at an angle this could provide distorted signals in that some signals entering the holes in the film at the beginning might not exit even though the hole was completely through the film. This would create an error which error would be enhanced as the film became thicker and/or the angle of the light increased.

It is preferable to use a light guide and a light guide sold under the tradename Lumatec can be used with the system of the present invention. Such a light guide has a 5 mm core diameter and a 1000 mm length. The light guide is selected due to its ability to transmit light of a wavelength in the range of about 300 to about 400 nm. The light guide assists in making the beam uniform at its exit face due to multiple bounces mixing rays within the fiber core guide region. The light guide ensures that the same amount of illuminating light is incident on each hole of the film. If a light source emits a uniform beam without a light guide the light guide could.be eliminated. The mechanical flexibility and length of light guide provide additional. degrees of freedom in order to address remote areas without the need for mirrors and relay lenses needed to obtain a free beam optical path. The light guide also makes it possible for the light source to be located at a distance away from the inspection area. This is a desirable feature although not a requirement.

It is also preferable to include an optical diffuser 3. The diffuser contributes to the uniformity of the beam on exiting the fiber. The diffuser consists of glass with gentle ripples on the surface on each side. Although the diffuser is not necessary some improvements in the accuracy of readings obtained could be expected by the use of a diffuser. A particularly preferred diffuser is the Coherent-Ealing glass diffuser.

The system also preferably includes an illuminating lens 4. A particularly preferred lens is sold under the name Melles-Griot which is a plano-convex, synthetic fused silica lens having a focal length of 25 mm. The lens collimates the beam coming from the light guide and directs the beam to the sample being inspected. It is also preferably to utilize spectral filters 5. Two spectral filters preferably used are sold under the tradename Schott Color Filter UG-11 and Schott Color Filter KG-3. This combination of spectral filters selects a 300 to 400 nm spectral band to be utilized for the inspection application for the holes on a Kapton film of the type described above. The UG-11essentially blocks a visible portion and the KG-3 blocks the infrared portion resulting in UV being transmitted through the filtered combination. These transmission filters or a more suitable spectrally selected mirror could be an integral part of the illumination source precluding the need for external filters.

Different filters or combinations of filters can be used in order to block light which might be transmitted through the membrane even though a pore is not present. Accordingly, such a filter or group of filters could be placed at any desired position between the light source and detector including immediately in front of the light source (i.e. before the porous membrane) or immediately in front of the light detector. Provided the material of the porous membrane is comprised of material which is not transparent to any of the light then the filters are not necessary. However, when the membrane is particularly thin (as is often the case) and comprised of polymer materials (as is often the case) light is transmitted or at least some wavelengths of light are transmitted. Accordingly, to obtain accurate readings the filters are used to filter out the light which would be transmitted through the membrane even though a pore is not present.

Light passing through the system porous membrane may pass directly onto the light detector 8. It is preferable that the light first pass through an imaging lens. A suitable imaging lens is sold under the trade name Melles-Griot symmetric-convex fused silica lens. This lens has a focal length of 50 mm. The imaging lens focuses the light transmitted through the porous membrane to the detection element 8. The lens is not highly corrected for lens aberrations due to cost considerations. Custom lens designs could be utilized but would be more costly than commercially available lenses. Further, many of the different lens materials utilized in custom lens designs do not transmit ultraviolet light with high efficiency. Accordingly, simple and cost-effective solution was the selection of the simple single element lens which is held within the light containment tube 13.

After passing through the imaging lens 6 the light preferably passes through an aperture stop 7. A useful aperture stop is a variable iris sold by Thorlabs. The aperture stop is used to sharpen the resolution as needed. The smaller the aperture the greater the ability to reduce the effects of lens aberrations. Thus, the aperture is needed less if the lens includes no aberrations. By closing the aperture down it is possible to sharpen the image. This is especially useful for imaging lenses that are not corrected for off-axis rays such as the single element lenses described above.

After passing through the aperture 7 and the light contacts the light detection element 8. A useful light detector is sold by Sony and is a black and white CCD sold as model XC-75CE. The detection element is typically a standard charge-coupled device (CCD) of the type used in cameras which capture a two-dimensional image and allow computer image processing to be performed on the signal detected. A typical CCD is the type used in an eight bit camera having 256 gray levels available per pixel. Cameras with greater or lesser than eight bits may also be used. A typical CCD chip in a camera has a size of about 4.8 mm vertically and 6.4 mm horizontally containing 439,992 pixels. Each of the pixels is about 8.6 microns wide by about 8.3 microns vertically and there are 756 pixels horizontally and 582 pixels vertically. The configuration described here is a common CCD configuration used in cameras and provides a cost effective system. When the imaging lens is located for unity magnification: (1:1 imaging) the area which can be inspected is equal to the active area of the detection element. At this magnification it is possible to separate the bright spots in the image by a distance of approximately 5 pixels. If there are less than 5 pixels between bright spots the spots begin to blur together and the ability to correctly count the number of holes is compromised.

The information obtained from the detector 8 is forwarded to the microprocessor 9. A useful image acquisition and processing unit is Checkpoint 900C. by Cognex. The frame grabber is a computer expansional electronics board which converts the image signal from the light detector 8 to a digital array of numbers consisting of gray levels and their pixel location in the two-dimensional image. This makes it possible for computer processing of the array of numbers (image processing). Blob analysis is a typical image processing tool which is widely available commercially. This type of processing detects whether many bright pixels are adjacent to one another. Then the tool can count the number of Blobs within an image that are above a pre-specified threshold. The number of Blobs typically corresponds to the number of holes in the inspection sample. Another image processing tool which could be used is referred to as a "light meter" or "mean pixel value" which sums the gray levels of all of the pixels within a particular pre-specified region of interest (ROI) and calculates the average.

SIMULTANEOUS MANUFACTURE AND ANALYSIS

The present invention is directed towards analysis of perforations in a material. In general, the method is used to scan a porous membrane which includes a plurality of pores and make an analysis as to whether or not the membrane passes or fails based on an analysis of a plurality of pores with consideration to a plurality of criteria simultaneously. Thus, in general, the invention does not individually inspect individual holes and analyze a pass/fail feature or criteria of each hole although such is possible in connection with the method of the invention.

The invention is also designed so that porous membranes can be analyzed sequentially. More specifically, the device for analyzing the membranes can include a means for holding the membrane in place while it is analyzed and a means for moving one membrane after another into an inspection position. This type of consecutive inspection/analysis procedure is useful during manufacturing. However, this method does not specifically effect the manufacturing other than to indicate that a membrane either passes or fails the inspection analysis.

In an alternative embodiment the invention can be designed so that it specifically effects the actual manufacturing process. Specifically, the method is used to analyze each hole or pore as it is created. Specifically, the pores created in the membrane by any suitable means such as the focused energy of a laser. While the laser energy is being applied the detector component and analytical device of the invention is placed on the side of the membrane opposite the side from which the laser is directed to the membrane. As the laser drills through the membrane light from the laser (or possibly another source) begins to impact the detector. When the detector notes that the desired amount of light is being detected which amount corresponds to the desired pore size and shape the laser energy is turned off. In this manner it is possible to repeatedly and accurately produce pores of a very small size in a very thin membrane. In accordance with this method the detection/analytical components of the invention are integrated with the controlled laser. Thus, by this method of the invention the analysis and manufacture are truly carried out simultaneously and carried out in a manner which they complement each other. The method can be modified to simultaneously drill and analyze two, three or a plurality of holes at the same time.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

This experiment demonstrates the use of the method of the invention to inspect holes in a sample. A mercury arc lamp of the type commonly used for ultraviolet adhesive curing was used for the light source. The ultraviolet portion of the spectrum was specifically isolated between 300 and 400 nanometers utilizing appropriate reflective and transmissive optical filter elements well known to those skilled in the art. This ultraviolet portion consisted mainly of the strong emission line from mercury at 365 nanometers. The filtered light was guided via a commonly used liquid light guide which transmits near ultraviolet in the spectral range selected. At the output of the fiber, a diffuse reflectance glass was used to provide additional homogenization of the beam exiting the guide. A condensing lens was then used to collimate the light and illuminate the sample to be inspected. The sample was a polyimide film. Spectral filters were located in the collimated light to ensure the rejection of any detectable visible and infrared light which would transmit through the sample substrate. An imaging lens was positioned in back of the sample to provide an image onto a light detection element. This element was a charge-coupled device or CCD. In close proximity to the imaging lens was an aperture stop which, when closed down to a small diameter, produced a clearer image at the CCD. The image was displayed on a monitor and the image information stored into a computer image file. This image was processed in order to determine the number and size of features in the sample. For example, a nozzle with an array of hundreds of through holes appeared on the image as an array of bright spots. The number of spots in the image should correspond exactly to the number of holes designed into the part. The amount of light incident on the CCD from each hole is transformed into gray levels covering picture elements or pixels in the CCD. These gray levels ranged from 0 to 255 for 8-bit CCD cameras. The pixels corresponding to each hole were defined as a cell, and the sum of the pixel gray levels within each cell was determined and correlated with the size of the hole. Thus image processing enabled the determination of both the number and size of the holes in the array.

Example 2

This experiment demonstrates the use of the method of the invention to inspect holes in a sample. A mercury arc lamp of the type commonly used for ultraviolet adhesive curing was used for the light source. The ultraviolet portion of the spectrum was specifically isolated between 300 and 400 nanometers utilizing appropriate reflective and transmissive optical filter elements well known to those skilled in the art. This ultraviolet portion consisted mainly of the strong emission line from mercury at 365 nanometers. The filtered light was guided via a commonly used liquid light guide which transmits near ultraviolet in the spectral range selected. At the output of the fiber, a diffuse reflectance glass was used to provide additional homogenization of the beam exiting the guide. A condensing lens was then used to collimate the light and illuminate the sample to be inspected. The sample was a polyimide film. Spectral filters were located in the collimated light to ensure the rejection of any detectable visible and infrared light which would transmit through the sample substrate. An imaging lens was positioned in back of the sample to provide an image onto a light detection element. This element was a charge-coupled device or CCD. In close proximity to the imaging lens was an aperture stop which, when closed down to a small diameter, produced a clearer image at the CCD. The image was displayed on a monitor and the image information stored into a computer image file. This image was processed in order to determine the number and size of features in the sample. For example, a nozzle with an array of hundreds of through holes appeared on the image as an array of bright spots. The number of spots in the image should correspond exactly to the number of holes designed into the part. The amount of light incident on the CCD from each hole is transformed into gray levels covering picture elements or pixels in the CCD. These gray levels ranged from 0 to 255 for 8-bit CCD cameras. A region of interest encompassing an entire array of holes is identified. The light meter tool is used to determine the average light level transmitted by the array of holes. This light level corresponds to an average calibrated hole size for the array.

What is claimed is:

1. A method of manufacturing a porous membrane, comprising:
   directing light energy at a surface of membrane material in an amount sufficient to create a pore in the material;
   detecting light passing through the pore; and
   analyzing the detected light in a manner so as to determine a criteria of the pore.

2. A non-destructive method of analyzing a porous membrane, comprising:
   directing light onto a porous membrane in an inspection position wherein the membrane is comprised of a layer of material having a plurality of pores therein wherein the light is characterized by having an intensity and a wavelength such that the material blocks a range of wavelengths of light and further wherein light entering pores will pass through the pores;
   detecting light passing through pores of the membrane;
   analyzing the detected light in a manner such that the analysis determines if pores of the membrane meet a criterion selected from the group consisting of a criteria which is a function of pore size and pore density, a criteria which is a function of the number of pores in the membrane, and a criteria which is a function of the shape of the pores in the membrane; and filtering light after the light leaves a light source and prior to a point where the light is detected and wherein the light is directed onto the porous membrane using a light guide means.

3. The method of claim 2, wherein the analyzing is carried out to determine if the plurality of pores collectively meets certain criteria.

4. The method of claim 2, wherein the pores have a pore diameter in the range of 0.01 microns to 100 microns.

5. A device for analyzing a porous membrane, comprising:
   a means for directing light onto a porous membrane, said means including a light source associated with a light guide and a filter;
   a means for detecting light passing through pores of the porous membrane;
   a means for analyzing detected light in a manner such that analysis determines if pores of the membrane meet a criteria; and
   a means for continuously repositioning the porous membrane relative to the device so as to continuously analyze porous membranes.

6. The device of claim 5, wherein the means for directing light is selected from the group consisting of UV laser and a mercury lamp source and pores having a diameter of less than 100 microns.

7. The device of claim 5, wherein the means for analyzing detected light is selected from the group consisting of a photo diode and a charge-coupled device.

8. The device of claim 5, wherein the means for continuously repositioning is a means for moving one porous membrane after another into a position where light is directed onto each membrane.

9. A method of analyzing a porous membrane, comprising:
   directing light onto a porous membrane in an inspection position wherein the membrane is comprised of a layer of material having a pore therein wherein the light is characterized by having an intensity and wavelength such that the material reflects light contacting its surface and further wherein light entering the pore will pass through the pore;
   detecting light reflecting off the material; and
   analyzing the detected light in a manner such that analysis determines if the pore of the membrane meets a criteria.

10. A method of analyzing a porous membrane, comprising:
    providing light to be directed onto a porous membrane in an inspection position wherein the membrane comprises a layer of material having at least one pore therein wherein the light is characterized by having an intensity and wavelengths such that at least some of the wavelengths will transmit through the material if exposed directly onto a surface of the material and further wherein light entering the pore will pass through the at least one pore;
    directing the light through one or more filters to filter out wavelengths of the light capable of transmitting through the material;
    directing the filtered light onto the porous membrane;
    detecting light passing through the at least one pore of the porous membrane; and
    analyzing the detected light in a manner such that analysis determines if the pore of the membrane meets a criteria.

11. A method of analyzing a porous membrane, comprising:
    directing light onto a porous membrane in an inspection position wherein the membrane is comprised of a layer of material having a pore therein wherein the light is characterized by having an intensity and wavelength such that the material blocks a range of wavelengths of light contacting its surface and further wherein light entering the pore will pass through the pore;
    detecting light passing through the pore of the porous membrane; and
    analyzing the detected light in a manner such that analysis determines if the pore of the membrane meets a criteria, wherein the analyzing includes an image process selected from the group consisting of blob analysis, light meter analysis and mean pixel value analysis.

12. The device of claim 5, wherein the means for repositioning comprises a first cylinder upon which inspected membranes are wound and a second cylinder from which membranes are unwound and positioned for inspection.

13. A method of manufacturing a porous membrane, comprising the steps of:
   directing energy at a surface of a membrane material in an amount sufficient to create a pore through the material;
   detecting energy passing through the pore; and
   analyzing the detected energy in a manner so as to determine a criterion of the pore.

14. The method of claim 13, further comprising the step of discontinuing the directing of energy at the surface of the membrane when the criterion has been met.

15. A method of manufacturing a porous membrane, comprising the steps of:
   applying energy to a surface of a membrane material in an amount sufficient to create a pore through the material;
   detecting energy passing through the pore; and
   discontinuing the application of energy when a desired amount of energy is detected which corresponds to a criteria of the pore.

16. The method of claim 15 wherein the criteria includes a desired pore size.

17. The method of claim 16 wherein the desired pore size is characterized by the pore having an unflexed exit aperture diameter in the range of 0.01 microns to 100 microns.

18. The method of claim 17 wherein the desired pore size is characterized by the pore having an unflexed exit aperture diameter in the range of 5 microns to 50 microns.

19. The method of claim 18 wherein the desired pore size is characterized by the pore having an unflexed exit aperture diameter in the range of 7.5 microns to 25 microns.

20. The method of claim 18 wherein the criteria includes a desired pore shape.

21. The method of claim 20 wherein the desired pore shape is substantially circular.

22. A method of analyzing a porous membrane used for aerosol drug delivery, said method comprising the steps of:
   directing light onto a porous membrane in an inspection position wherein the membrane is comprised of a layer of material having a pore therein wherein the light is characterized by having an intensity and wavelength such that a filter disposed between the material and the light blocks a range of wavelengths of light contacting the material surface and further wherein light entering the pore will pass through the pore;

detecting light passing through the pore of the porous membrane; and analyzing the detected light in a manner such that analysis determines if the pore of the membrane meets a criterion which is a function of pore size.

23. A method of analyzing a porous membrane, said method comprising the steps of:

providing a porous membrane material having a pore, wherein the membrane material is visible light transmissible at wavelengths greater than about 550 nm;

directing energy onto the porous membrane in an inspection position whereby energy entering the pore will pass through the pore;

detecting energy passing through the pore; and analyzing the detected energy in a manner such that analysis determines if the pore of the membrane meets a criterion.

24. The method of claim 23, wherein the energy comprises wavelengths less than about 550 nm.

25. The energy of claim 23, wherein the energy directed onto the porous membrane consists of energy having wavelength less than about 450 nm.

26. The method of claim 23 wherein the membrane material is polyimide.

27. The method of claim 23 wherein membrane material is about 25 microns thick.

28. The method of claim 1, wherein the analysis of the detected light determines the size of the pore.

29. The method of claim 28, further comprising:

discontinuing the direction of light energy at the surface of the membrane material in the location of the pore when the analysis has determined that the pore has reached a predetermined size.

30. The method of claim 1, wherein the light energy directed is laser light.

31. A method of manufacturing a porous membrane, comprising:

directing light energy at a surface of a membrane material in an amount sufficient to create a pore in the material;

detecting light passing through the membrane material opposite the surface at which the light energy is directed; and analyzing the detected light to determine a criterion of a pore being formed.

32. The method of claim 31, wherein the analysis of the detected light determines whether a pore has been formed completely through the membrane material.

33. The method of claim 31, wherein the analysis of the detected light determines the size of the pore.

34. The method of claim 31, further comprising:

discontinuing the direction of light energy at the surface of the membrane material in the location of the pore when the analysis has determined that a predetermined criterion of the pore has been met.

35. The method of claim 34, wherein the predetermined criterion is a predetermined size of the pore.

36. A method of simultaneously manufacturing and inspecting a porous membrane, comprising:

directing light energy at at least one location on a surface of a membrane material in an amount sufficient to create a pore in the material;

detecting light passing through the membrane material opposite each location on the surface at which the light energy is directed; and analyzing the detected light to determine at least one criterion of at least one pore being formed.

37. The method of claim 36, wherein the analysis determined the size and shape of the at least one pore.

38. The method of claim 37, further comprising discontinuing the direction of light at the location corresponding to where a pore having a predetermined size and shape is determined, by analysis, to have been formed.

39. The method of claim 36, wherein the light is directed at a plurality of locations on the surface to form a plurality of pores simultaneously.

40. The method of claim 36, wherein the light is directed at a plurality of locations and the analyzing is carried out to determine at least one of the criteria selected from the group consisting of: whether the holes have been made through the membrane material; whether the holes made have sufficient size; and whether the holes made provide a sufficient pore density.

41. The method of claim 40, further comprising discontinuing the direction of light when the analysis determines that the criteria have been met.

42. The method of claim 36, wherein the light that is directed is laser light.

43. A system for manufacturing and analyzing a porous membrane, comprising:
- a light source capable of directing light onto the surface of a membrane material in an amount sufficient to drill at least one pore in the membrane material:
- a light detector adapted to be positioned adjacent the membrane material on a side of the membrane material which is opposite the surface at which the light is directed; and
- a microprocessor electrically connected to said light source and said light detector; said microprocessor being adapted to analyze light passing through said membrane material and said at least one pore, when formed; said microprocessor providing feedback to said light source to discontinue direction of light when at least one pore having predetermined criteria has been formed as determined by the light analysis.

44. The system of claim 43, further comprising at least one light guide positioned to direct light from said light source to the membrane material.

45. The system of claim 43, further comprising an optical diffuser adapted to be placed in the directed light between the light source and the membrane material.

46. The system of claim 43, further comprising an illuminated lens adapted to be placed in the directed light between the light source and the membrane material.

47. The system of claim 43, further comprising at least one spectral filter adapted to be placed in the directed light between the light source and the membrane material.

48. The system of claim 43, wherein said light detector comprises a charge-coupled device.

49. The system of claim 43, further comprising an imaging lens adapted to be positioned between the membrane material and said light detector.

50. The system of claim 49, further comprising an aperture stop positioned between said imaging lens and said light detector.

* * * * *